(12) United States Patent
Wiksell et al.

(10) Patent No.: US 8,652,124 B2
(45) Date of Patent: Feb. 18, 2014

(54) ANTI-SEEDING ARRANGEMENT

(75) Inventors: Hans Wiksell, Täby (SE); Gert Auer, Solna (SE); Vilhelm Ekstrand, Nacka (SE)

(73) Assignee: Neodynamics AB, Lidingo (SE)

( * ) Notice: Subject to any disclaimer, the term of this patent is extended or adjusted under 35 U.S.C. 154(b) by 842 days.

(21) Appl. No.: 12/294,671

(22) PCT Filed: Mar. 5, 2007

(86) PCT No.: PCT/EP2007/052058
§ 371 (c)(1),
(2), (4) Date: Dec. 8, 2008

(87) PCT Pub. No.: WO2007/110299
PCT Pub. Date: Oct. 4, 2007

(65) Prior Publication Data
US 2010/0228242 A1   Sep. 9, 2010

(30) Foreign Application Priority Data
Mar. 28, 2006 (EP) ..................................... 06006361

(51) Int. Cl.
*A61B 18/04* (2006.01)
(52) U.S. Cl.
USPC ........................................................... 606/33
(58) Field of Classification Search
USPC ......... 606/33, 34, 200, 45, 32, 35, 37, 40, 41, 606/42, 49
See application file for complete search history.

(56) References Cited

U.S. PATENT DOCUMENTS

| | | | |
|---|---|---|---|
| 5,423,809 A | 6/1995 | Klicek et al. ................... | 606/38 |
| 6,162,216 A | 12/2000 | Guziak et al. .................. | 606/34 |
| 6,267,757 B1 * | 7/2001 | Aita et al. ....................... | 606/33 |
| 2003/0109802 A1 | 6/2003 | Laeseke et al. | |
| 2003/0130711 A1 | 7/2003 | Pearson et al. | |
| 2003/0171744 A1 | 9/2003 | Leung et al. .................... | 606/41 |
| 2003/0195500 A1 | 10/2003 | Moorman et al. .............. | 606/33 |
| 2003/0212394 A1 | 11/2003 | Pearson et al. | |

(Continued)

FOREIGN PATENT DOCUMENTS

EP    1 839 581 A1    3/2007

OTHER PUBLICATIONS

International Search Report with Written Opinion in PCT Application No. PCT/EP2007/052058, dated Jun. 20, 2007, 11 pages.

*Primary Examiner* — Nicholas Lucchesi
*Assistant Examiner* — Brooke Matney
(74) *Attorney, Agent, or Firm* — Harrity & Harrity, LLP

(57) ABSTRACT

The present invention relates to an anti-seeding arrangement (100) for invasive treatment of a human or animal body comprising an elongated hollow member (102), and a first electrode (116) of which one portion is arranged near one end of the elongated hollow member (102), said first electrode (116) being connectable to an electromagnetic field generator (110), wherein the elongated hollow member (102) is arranged to be inserted into the human or animal body, control means (106, 108) arranged to control the electromagnetic field generator (110) for delivering radio frequency bursts to the first electrode (116), and sensing means (104) to sense a physical property dependent on the insertion length of the elongated hollow member (102) in the human or animal body, and wherein the control means (106, 108) is arranged to control the operation of the electromagnetic field generator (110) in dependence of the sensed physical property.

23 Claims, 1 Drawing Sheet

(56) References Cited

U.S. PATENT DOCUMENTS

| | | | |
|---|---|---|---|
| 2004/0097920 A1 | 5/2004 | Desinger | 606/45 |
| 2004/0186422 A1 | 9/2004 | Rioux et al. | 606/44 |
| 2004/0230262 A1* | 11/2004 | Sartor et al. | 607/96 |
| 2005/0075629 A1 | 4/2005 | Chapelon et al. | 606/41 |

* cited by examiner

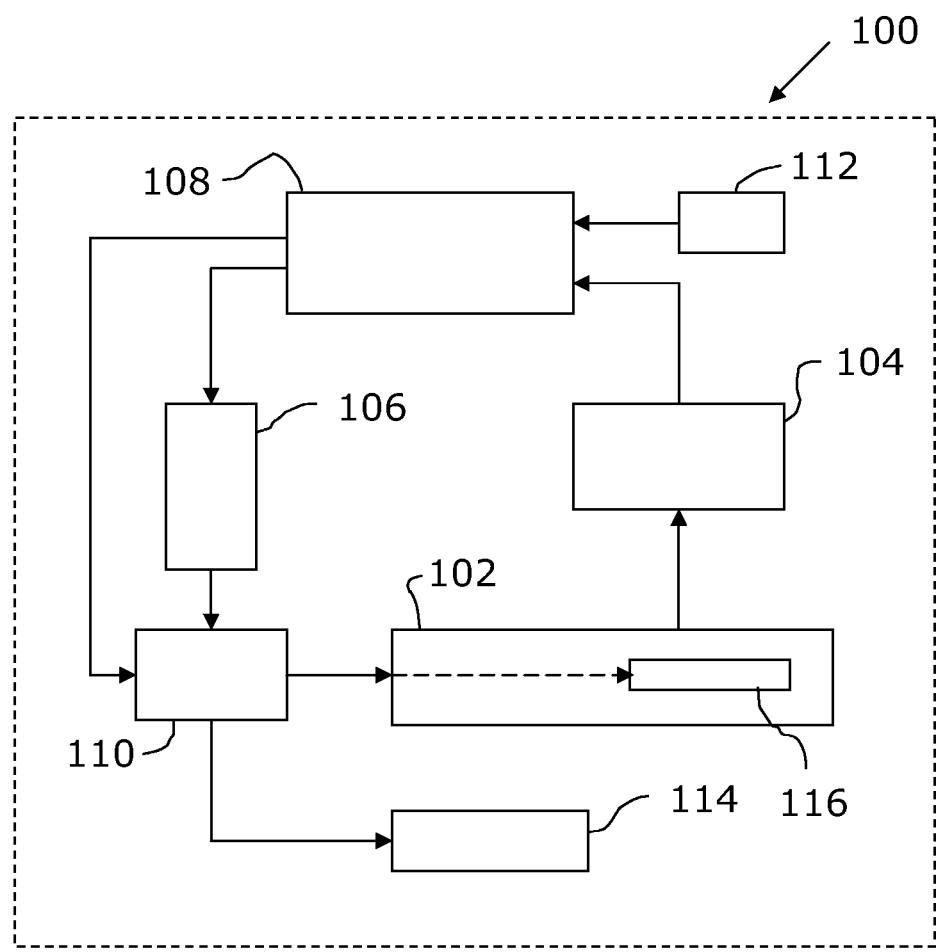

ANTI-SEEDING ARRANGEMENT

The present invention relates in general to providing an arrangement for invasive operations in human or animal bodies, and especially to providing an arrangement for anti-seeding in connection to invasive operations in human or animal bodies.

DESCRIPTION OF RELATED ART

Many people in the western world face the prospect of cancer. The most common cancer forms in females and males are breast cancer and prostatic cancer, respectively.

A successful cancer therapy is often dependent on a high quality tumour diagnosis. There are today two major methods of morphological diagnosis. These are histopathological examination of surgical biopsies or core biopsies and cytopathological examination of fine needle aspirates.

In core biopsy, a tissue sample is removed from the lesion, for example by using a coarse core biopsy needle. This tissue sample is then examined histologically.

In cytological diagnosis, a suspension of cells is aspirated from the lesion with the aid of a fine needle. Since the adhesion between tumour cells is lower than the adhesion between healthy cells, tumour cells are enriched in the aspirate. Ongoing advances suggest that completely objective molecular diagnostic procedures on single cells from fine needle aspirates can be available in the near future.

Applying modern diagnosis, small tumours can be detected which have not yet metastased. For such cancer tumours, having an extension that typically is less than 10 mm, conventional surgery may be seen as too coarse a method.

Also, in therapy the tendency has been towards less invasive local treatment of the tumour and hence away from radical surgery such as mastectomy, in the breast cancer case. The goal of radical mastectomy is to remove all malignant tissue, which combined with lymph node resection, often results in considerable hospitalisation.

Minimally invasive approaches, in contrast to open surgery, have as potential benefits reduced morbidity rates, reduced treatment duration and provide the possibility to treat a patient in a weak medical condition.

One example of a minimally invasive therapy approach is the radio frequency ablation (RFA) technique which uses radio frequency energy to cause thermal destruction of tumour cells. The destruction can be obtained by, for example, inserting a needle directly in the tumour, arranging a large counter electrode to an outer surface of the body and applying radio frequency energy between the needle and the counter electrode. The high current density at the needle generates heat in the tissue, causing thermal destruction and/or denaturation of said tissue.

At present the RFA technique is most often viewed as being palliative and used to shrink the tumours such that surgery can be avoided.

Another minimally invasive approach is stereo tactic excision or large core biopsy, which is a surgical technique that preferably involves removing the entire breast lesion under image guidance. By using large core biopsy, breast tissue of the size of 5 mm to 20 mm may be removed. This procedure also allows the radiologist or surgeon to remove the entire lesion in one non-fragmented piece. The core specimen of the breast tissue is often removed with a looped wire and taken to the pathology laboratory for diagnosis.

Yet another minimally invasive approach that can be applied in diagnosis and therapy of body tissue is infusion of diagnostic and therapeutic agents to a site within a tissue. By inserting a needle reaching an invasive site, and presenting the needle tip to the tissue site, a site-specific delivery of diagnostic and therapeutic agents to said tissue site is enabled.

Yet other minimally invasive techniques that may be used for the same or similar purposes are endoscopic procedures, wherein tubular devices are percutaneously inserted in a body to reach an invasive site in need for surgical operation or investigation. In short, tissue may hence be resected, visually examined and sampled without open surgery.

The techniques and methods for diagnosis and/or therapy of tissue as mentioned above have the common denominator of involving a touching or puncturing malignant tissue by at least one part of the device being used.

In addition, said techniques and methods may also touch or puncture local infections.

By puncturing and/or manipulating malignant tissue, cancer cells can be disrupted from their original position and deposed in other places.

Disruption and disposition of cancer cells may further give rise to seeding of cancer cells in the tract formed by the equipment being used, considered that some part, for instance the distal end of a needle, of the equipment penetrates or contacts the malignant tissue. Upon penetration or contacting by the distal end of malignant tissue, said distal end becomes contaminated with non-healthy cells. Upon removal of the equipment, the contaminated distal end is slid along the tract/channel that was formed upon insertion, malignant tissue cells may come loose from the contaminated distal end or the malignant tissue as such and may be repositioned onto the walls of the tract/channel, thereby causing the seeding of the tumour.

This seeding of cancer cells may give rise to new cancer tumours.

Tumour seeding may thus be result of core biopsy, laparoscopy, radio frequency ablation, injection, and fine needle aspiration or punctuation etc. and can therefore negate the benefits of the operation involved.

For obvious reasons, seeding of local infectious matter may also occur during the above operations. This is of special importance during trans-rectal procedures of for example the prostate.

In the following, prior art documents related to potential spread of un-healthy cells are presented.

From US 2004/0186422 A1 a needle for delivering therapeutic or diagnostic agents in a target site in a body is known. The needle may be provided with an electrode that is coupled to a radio frequency generator. By delivering electrical energy from at least a portion of the needle to tissue surrounding at least a portion of the tract, the surrounding tissue may coagulate, be ablated or otherwise treat the surrounding tissue to substantially seal or occlude the tract. Electrical energy may be delivered to additional tissue along the tract in short bursts such that spaced-apart regions can be treated. Alternatively, energy is delivered substantially continuously upon withdrawal of the needle to substantially seal the tract along its entire length. The tract may thus be substantially sealed lowering the risk of tracking seeding from a tumour and/or contaminating tissue surrounding a target region to which an agent is delivered.

One disadvantageous property of this technique is that the delivered radio frequency energy heats the tissue surrounding the track such that tissue of a relatively large depth is affected by the high temperature produced.

Another disadvantage of the diagnostic equipment of this technique is that sample tissue in the needle is also affected by the heating caused by the radio frequency energy.

A potential disadvantage of the technique of US 2004/0186422 A1 is associated with the application of the short bursts or continuous radio frequency energy to substantially seal the track when the needle or instrument is being retracted. Since the technique is operated manually and the needle is typically held and retracted by an operator, there is a risk that viable cells will remain in the track after the application of the radio frequency energy when retracting the needle, since the result of treating the tract is dependent of the skill of the operator using this technique.

Another potential disadvantage with the regime of US 2004/0186422 A1 is there is no solution to disruption of tumour cells when the inserted instrument penetrates through the tumour, potentially leading to seeding of tumour cells.

In addition, since the technique is operated manually, the technique is time consuming in general and consumes time for an operator in particular, which are disadvantageous.

From US 2003/0195500 it is known a modular biopsy ablation or track coagulation needle comprising an outer tubular member and an inner member which allows a biopsy needle to be inserted into, and coaxially engaged with, a delivery needle and removed when not needed. It also allows to more efficiently biopsy a tumour, ablate it and coagulate the track by ablation while reducing the track seeding and blood loss. The ablation needle and biopsy needle forms a connector arranged to be coupled to an electric ablating source.

In the case of track ablation, an isotherm of 48° C. is suggested which extends 1 mm radially from the track into the tissue. In the case of tumour ablation the isotherm of 48° C. is suggested to have a radical extension of 20 mm, which is being achieved by using a higher microwave power or a different microwave frequency, as compared to the track ablation case.

A clear disadvantage with the technique as disclosed by US 2003/0195500 is that this device uses microwave frequency energy. A consequence of using microwave frequencies is that a comparatively large tissue region is heated, where said region also comprises healthy tissue in no need of treatment, which clearly is non-beneficial.

Another disadvantage of the US 2003/0195500 technique is that coagulation of the entire track requires multiple applications of micro-wave energy, where the delivery needle is rejected piece-wise, and where microwave frequencies are applied to the delivery needle in between the rejections, due to the fact that each application of the microwave energy of the power being used to achieve the isotherms as mentioned above, lasts a relatively long time.

Moreover, manual operation of this regime brings the disadvantage of risking that viable cells remain in the track subsequent to the application of micro-wave energy, since the tissue surrounding the track is often non-homogenous and therefore require different applications of energy to ablate the track.

Yet another disadvantage is that energy absorption upon application of microwave frequency is often non-homogenous, which can result in spots being over-heated, so called "hot spots".

From U.S. Pat. No. 6,126,216 it is known a medical instrument comprising a cannula or probe that is used to penetrate tissue to a target area to be used in medical procedures including biopsy and radio frequency ablation of undesirable tissues or cells for treatment of or to prevent the spread of cancer cells during a biopsy procedure.

The exterior surface of the probe has a dielectric coating, and control means for adjusting the electric current to the cannula, a radio frequency generator and a return electrode. By generating radio frequency energy, the cannula is heated above a critical temperature causing the tissue surrounding the cannula to become non-viable.

The disclosure of U.S. Pat. No. 6,126,216 comprises a first application being a biopsy needle, for which ablative radio frequency energy is claimed to be delivered to the tissue to provide resistive heating approximately 10 cell layers deep around the cannula. No information is provided to support this cell layer performance.

One drawback with the biopsy needle technique as disclosed in U.S. Pat. No. 6,126,216 is the application of radio frequency energy which is applied to achieve elevated temperature in tissue of a depth of approximately 10 cell layers.

To our understanding, the radio frequency energy is applied by applying a current having a very low current density in order to restrict the temperature rise to a depth of approximately 10 cell layers. Using a low current density however requires a long duration of application of the radio frequency energy, which for this reason is a clear drawback since the rise in temperature during that duration will be influenced by heat conduction to neighbouring tissues and thereby also by blood perfusion and other tissue properties.

Another drawback of the technique as disclosed by U.S. Pat. No. 6,126,216 is the skin burn effect that is caused due to the contact between the electrode and the skin upon penetrating the skin by the biopsy needle, upon application of radio frequency energy to the biopsy needle. The usage of the entire shaft of the needle as an electrode thus results in undesired skin burn effects.

A potential drawback of the technique of U.S. Pat. No. 6,126,216 is that full penetration of a tumour by the electrode may result in dislocated viable tumour cells that could proliferate in healthy tissue into new cancer tumours.

Conclusively, a common disadvantage of the prior art techniques and disclosures is that movement of inserted instruments in longitudinal directions may result in non-complete track tumour cell killing.

In addition, continuous application of energy may result in an unnecessarily large diameter of tissue killing that the sample in the needle is affected as well as an increased operation time.

There is thus a need for providing a more efficient anti-seeding device free from the disadvantages and drawbacks that are associated with the prior art techniques.

SUMMARY OF THE INVENTION

It is an object of the present invention to provide an anti-seeding arrangement enabling a complete anti-seeding treatment.

According to one aspect of this invention, this object is achieved by the arrangement for invasive treatment of a human or animal body comprising an elongated hollow member having two ends, and a first electrode of which at least one portion is arranged at least near one end of the elongated hollow member, said first electrode being connectable to an electromagnetic field generator, wherein the elongated hollow member is arranged to be at least partly inserted into the human or animal body, sensing means arranged to sense a physical property of the arrangement, which physical property is being dependent on at least of the insertion length of the elongated hollow member in the human or animal body, and control means arranged to control the electromagnetic field generator for delivering radio frequency bursts to the first electrode of the elongated hollow member, being connectable to an electromagnetic field generator, being arranged to control the operation of the electromagnetic field generator in dependence of the sensed physical property by the sensing means and comprising triggering means for triggering the electromagnetic field generator to deliver radio frequency bursts in dependence of variations of the sensed physical property.

A second aspect of the present invention is directed towards the arrangement for invasive treatment including the features of the first aspect, wherein the sensing means is arranged to sense the physical property optically, mechanically, acoustically, electrically or electromagnetically.

A third aspect of the present invention is directed towards the arrangement for invasive treatment including the features of the first aspect, wherein the sensing means comprises impedance sensing means.

This aspect of the present invention is advantageous since the impedance being an electrical quantity that is easily obtainable and convenient to utilize in electrical or electronic control means.

A fifth aspect of the present invention is directed towards the arrangement for invasive treatment including the features of the first aspect, further comprising a second electrode arranged to be connected to the electromagnetic field generator and arranged to be positioned on the human or animal body.

A sixth aspect of the present invention is directed towards the arrangement for invasive treatment including the features of the fifth aspect, wherein the impedance sensing means is arranged to sense an impedance at least related to the impedance between the second electrode and at least part of the first electrode.

This aspect of the present invention is advantageous since the impedance between the second electrode and at least part of the first electrode is easily measurable.

A seventh aspect of the present invention is directed towards the arrangement for invasive treatment including the features of the first aspect, wherein the sensing means is arranged to sense the distance from a reference point for the elongated hollow member to the surface of the tissue into which the elongated hollow member is arranged to be at least partly inserted.

An eighth aspect of the present invention is directed towards the arrangement for invasive treatment including the features of the first aspect, wherein the control means is arranged to be connected to the sensing means.

A ninth aspect of the present invention is directed towards the arrangement for invasive treatment including the features of the first aspect, wherein the control means is arranged to control the operation of the electromagnetic field generator such that radio frequency bursts are delivered from the electromagnetic field generator in dependence of variations of the sensed physical property value.

This aspect of the present invention is advantageous since making the electromagnetic field generator deliver radio frequency energy in dependence of the variations of the sensed physical property enables a rapid response to movements of the elongated hollow member.

A tenth aspect of the present invention is directed towards the arrangement for invasive treatment including the features of the first aspect, wherein the arrangement further comprises the electromagnetic field generator, and wherein the electromagnetic field generator is arranged to deliver radio frequency bursts.

An eleventh aspect of the present invention is directed towards the arrangement for invasive treatment including the features of the first aspect, wherein the first electrode is located at one end of the elongated hollow member.

A twelfth aspect of the present invention is directed towards the arrangement for invasive treatment including the features of the first aspect, wherein the elongated hollow member comprises a region that is electrically insulated in relation to the first electrode.

This aspect of the present invention is advantageous since it provides protection against skin burn effects upon operation of the arrangement of the present invention.

A thirteenth aspect of the present invention is directed towards the arrangement for invasive treatment including the features of the twelfth aspect, wherein the insulating region is situated near the other end of the elongated hollow member.

A fourteenth aspect of the present invention is directed towards the arrangement for invasive treatment including the features of the thirteenth aspect, wherein the insulating region comprises a hollow insulating sheath being longitudinally movable over the first electrode.

This aspect of the present invention is advantageous since the insulating sheath enables quick variation of the effective length of the first electrode in the tissue.

A fifteenth aspect of the present invention is directed towards the arrangement for invasive treatment including the features of the first aspect, wherein the first electrode is longitudinally segmented.

This aspect of the present invention is advantageous since segmentation may provide protection against skin burn effects, as well as enable variation of the effective length of the first electrode.

A sixteenth aspect of the present invention is directed towards the arrangement for invasive treatment including the features of the first aspect, wherein the elongated hollow member is coated with a dielectric material.

This aspect of the present invention is advantageous since ablation by part of an elongated hollow member may be achieved at one radio frequency and anti-seeding of the entire track may be achieved using the same elongated hollow member at a different frequency A seventeenth aspect of the present invention is directed towards the arrangement for invasive treatment including the features of the sixteenth aspect, wherein the radio frequency bursts are generated at one or more radio frequencies.

An eighteenth aspect of the present invention is directed towards the arrangement for invasive treatment including the features of the first aspect, wherein the elongated hollow member comprises a needle arranged for fine needle aspiration or injection.

This aspect of the present invention is advantageous since it provides anti-seeding to fine aspiration or injection needles.

A nineteenth aspect of the present invention is directed towards the arrangement for invasive treatment including the features of the first aspect, wherein the elongated hollow member further comprises a solid member insertable into the hollow member, wherein both are arranged for biopsy operations.

This aspect of the present invention is advantageous since it provides anti-seeding to elongated hollow members used in biopsy operations.

A twentieth aspect of the present invention is directed towards the arrangement for invasive treatment including the features of the first aspect, wherein the elongated hollow member is arranged for radio frequency ablation of tissue of human or animal body.

This aspect of the present invention is advantageous since it provides anti-seeding to elongated hollow members used in ablation.

A twenty-first aspect of the present invention is directed towards the arrangement for invasive treatment including the features of the first aspect, wherein the elongated hollow member is arranged for endoscopic operations.

This aspect of the present invention is advantageous since it provides anti-seeding to elongated hollow members used for endoscopic operations.

The present invention has the following overall advantages:

Application of sensing means for the detection of movement of the elongated hollow member together with the usage of radio frequency power creating an essentially instantaneous denaturation of tissue surrounding an anti-seeding electrode, provides a rapid arrangement for anti-seeding without being directed towards time consuming alternatives as presented by the prior art. The invention is also advantageous since the rapid response will be dependent on the triggering of the electromagnetic field generator.

It should be emphasized that the term "comprises/comprising" when used in this specification is taken to specify the presence of stated features, integers, steps or components, but does not preclude the presence or addition of one or more other features, integers, steps, components or groups thereof.

BRIEF DESCRIPTION OF THE DRAWINGS

The present invention will now be described in more detail in relation to the enclosed drawings, in which:

FIG. 1 shows a schematical representation of an arrangement for invasive treatment according to one embodiment of the present invention.

DETAILED DESCRIPTION OF THE EMBODIMENTS

The present invention thus relates to an arrangement for treating a human or animal body in general, and to an arrangement for denaturating tissue, cells and infectious matter in a human or animal body in particular.

Since seeding or spreading of malignant cells, tissue or infectious matter is an evident risk when inserting medical equipment into a human or animal body site containing such matter, seeding may occur in various applications such as infusion, radio frequency ablation, fine needle aspiration, core biopsy as well as endoscopic procedures. For this reason and to enable a more efficient anti-seeding procedure the anti-seeding arrangement of the present invention is arranged to be utilized in every one of the applications as mentioned above, that is in infusion, in radio frequency ablation, in fine needle aspiration, in core biopsy as well as in endoscopic procedures.

Whenever a member is passed through healthy tissue after the management of infectious or malign tissue, it is desirable that the member is free from contamination With this aim radio frequency bursts are applied between a first electrode and a counter electrode in the present invention.

In general terms the arrangement for anti-seeding according to the present invention comprises an elongated hollow member that is adapted to be inserted into a tissue by puncturing the tissue with one end of the elongated hollow member.

In addition the arrangement comprises means for sensing longitudinal movement of the member relative to the tissue. Moreover the arrangement also comprises means for controlling an electromagnetic field generator such that radio frequency bursts of a relatively high power can be applied to the tissue by the elongated hollow member.

With reference to FIG. 1 schematically showing one representation of the arrangement for invasive treatment according to the present invention, the present invention will further be explained.

The representation in FIG. 1 of the arrangement 100 comprises an elongated hollow member 102, which may be adapted to specific applications of this invention, as will be described down below and which further is arranged to be at least partially inserted in a human or animal body. The arrangement 100 further comprises sensing means 104 coupled to the elongated hollow member 102 and arranged to be used when determining the insertion length of the elongated hollow member 102 in a human or animal body, and a control unit 108 to which the sensing unit 104 and a user input unit 112, are connected. The control unit 108 is further connected to a triggering unit 106 and a radio frequency generator 110, where the triggering unit 106 is arranged to trigger the radio frequency generator 110 in dependence of input from the sensing unit 104 and the user input unit 112. The radio frequency generator 110 is further coupled to a first electrode 116 that is comprised by the elongated hollow member 102, and to a counter electrode 114, being one example of a second electrode.

The sensing unit 104 may be arranged to sense the impedance between the first electrode 116 of the elongated hollow member 102 and the counter plate 114, wherein the impedance is dependent of the insertion length of the elongated hollow member in the human or animal body. The impedance between the first electrode of the elongated hollow member and the counter plate typically decreases upon increasing the penetration depth in the human or animal body. This is due to that the contact surface between the first electrode and the surrounding tissue when penetrating the elongated hollow member is increased.

In an alternative embodiment of the present invention, the sensing unit 104 is arranged to sense the penetration depth of the elongated hollow member in the tissue, for instance the distance from a reference point for the elongated hollow member to the tissue surface, in a mechanical way.

In yet another embodiment of the present invention, the sensing unit 104 may be arranged to sense the penetration depth of the elongated hollow member in the tissue acoustically or electromagnetically, for instance by sensing the distance from a reference point for the elongated tubular member to the tissue surface.

According to still yet another embodiment of the present invention the sensing means and the control means may be integrally formed.

It should be emphasized that the arrangement as schematically shown in FIG. 1 is one representation of an arrangement of the present invention. Other representations which may comprise different units, and/or comprise units having combined functions as compared with the representation as shown in FIG. 1, are also envisaged.

The triggering unit 106 is thus arranged to be connected to the radio frequency generator 110 and to generate a trigger signal triggering the radio frequency generator to generate radio frequency energy. Moreover, the radio frequency generator 110 is arranged to generate radio frequency energy in the form of bursts having a duration of the order microseconds up to milliseconds depending on the used frequency in the bursts. The radio frequency generator is arranged to deliver such bursts at regular intervals having an off-duration of several orders of magnitude larger than the on-duration, wherein the on-duration equals to the burst length.

For this reason a relatively high power of radio frequency energy may be applied for the purpose of anti-seeding. The power that is applicable in each case is dependent on a number of parameters including the diameter of the elongated hollow member to be inserted in the tissue, the conductivity and characteristics of the tissue into which the member is to be inserted, the blood flow of the tissue, the shape and configuration of the electrode of the elongated hollow member etc.

Since the power dependency of the radius, R of an electrode is proportional to $R^4$, large electrodes require a high power, whereas anti-seeding using thin electrodes shows promising results using low or moderate power levels.

It is however possible to use high power radio frequency energy under certain circumstances, as indicated above. For instance peak power levels up to tens of kW may be used. Again by using an off-duration being several orders of magnitude larger than the on-duration, high power levels may be used in special circumstances. In general more modest power levels tailored for the case in point are used with which rapid highly efficient anti-seeding may be obtained.

The triggering unit 106 may be arranged to trigger the electromagnetic generator 110 to deliver electromagnetic energy to the first electrode, as the sensing unit senses a movement of the elongated hollow member 102. The elongated hollow member is either retracted manually or mechanically or may even be moved by a combined motion under both manual and mechanical influence. The electromagnetic energy can be delivered to the first electrode irrespective of how the elongated hollow member is retracted.

The radio frequency bursts as applied to the first electrode may thus be activated upon retraction of the elongated hollow member 102. In one alternative embodiment of the present invention the radio frequency bursts may be activated upon insertion of the elongated hollow member in the human or animal body.

Application of bursts or short pulses when using the arrangement 100 in relation to a lesion in a human or an animal body, enables the control of the application of radio frequency energy to the tissue such that the tissue region that is affected by radio frequency energy is a few cell layers thick around the first electrode 116.

Moreover, using sensing means for the control of the application of high power short pulses achieves substantially immediate tract killing enabling rapid movement of elongated hollow members 102 in the treated tissue, with unchanged anti-seeding performance.

Rapid and reliable tract killing or denaturation of a tissue site under investigation is thus enabled by using an elongated hollow member of the present invention and triggering of radio frequency bursts or anti-seeding pulses.

In one alternative embodiment of the present invention, the arrangement 100 may comprise means for longitudinal and/or rotational movements of the elongated hollow member. Such means may provide an oscillating longitudinal vibration and/or rotational movement of the elongated hollow member, wherein the movement has a frequency in the order of 50-500 Hz. Providing an oscillating longitudinal and/or rotational movement of the elongated hollow member 102 facilitates insertion of the elongated hollow member in the human or animal body as penetration resistance of the needle into the tumour during the insertion phase is decreased. It may also increase the sample volume.

Triggered anti-seeding is thus also needed during each vibrational retraction and insertion phase.

In addition to the advantage of denaturation possible cancer cells in the track caused upon insertion of the elongated hollow member, application of radio frequency energy brings the advantage of stopping potential bleeding from the lesion caused by the elongated hollow member.

In the following will the elongated hollow member be explained in more detail.

The elongated hollow member 102 typically has first and a second end. Upon usage of the elongated hollow member 102, that is for instance inserting the elongated hollow member in a human or animal body, these ends can be denoted the proximal end and a distal end, respectively. Moreover the first electrode may be arranged at the distal end of the elongated hollow member 102, according to one embodiment of the present invention. According to another embodiment of the present invention the first electrode is arranged near the distal end of the elongated hollow member 102. According to yet another embodiment of the present invention, the first electrode may be arranged at another position along the elongated hollow member 102.

According to yet another embodiment of the present invention the first electrode is arranged along the elongated hollow member in a way such that the first electrode 116 possesses a longitudinal extension, along the elongated hollow member 102.

According to one embodiment of the present invention the elongated hollow member 102 is arranged to be connected to the radio frequency generator 110, such that the first electrode 116 of the elongated hollow member 102 is connectable to the radio frequency generator 110.

According to yet another embodiment of the present invention the elongated hollow member 102 comprises an insulating sheath that is hollow and surrounds the elongated hollow member 102. The insulating sheath is electrically insulating and may therefore be used to insulate at least part of the first electrode from the surrounding tissue. The insulating sheath surrounding the elongated hollow member 102 is slideably movable in the longitudinal direction of the elongated hollow member 102. By sliding the insulating sheath along the elongated hollow member 102 over the first electrode, variation of the length of the first electrode is enabled. The effective length of the first electrode can thus be varied without moving the elongated hollow member in the longitudinal direction. Also the penetration depth of the first electrode in the tissue can be varied without altering the length of the first electrode that is subjected to the tissue, due to presence of the insulating sheath.

Moreover, by letting the slidedable insulating sheath at least surround the first electrode at the air-skin interface upon operating, an unfavourable skin burn effect can effectively be avoided. The design of the slidable sheath may thus be such that a first part is arranged to be insertable in the tissue surrounding the first electrode and a second part is arranged to hinder further penetration of the second part in the tissue. This second part for instance in the form of a flange or a collar is arranged to contact the tissue surface, that is the skin, whereas the first part of the sheath is arranged to penetrate the skin of the tissue, to avoid such a skin burn effect.

According to one alternative of the present invention the first electrode may be segmented in the longitudinal direction of the elongated hollow member 102, that is along the elongated hollow member. Upon insertion of such a elongated hollow member having a segmented first electrode, in a tissue, a few of the electrode segments may be surrounded by body tissue, whereas others may still face the surrounding air by being outside of the body tissue, dependent on the insertion length of the elongated hollow member 102.

Since some electrode segments will be within the body and other will not, the impedance between the electrode segments of the first electrode of the elongated hollow member and the counter electrode will vary in relation to the insertion depth of the elongated hollow member in the tissue. Whereas the impedance between the segments facing air and the counter electrode is essentially infinite, the impedance between a segment being penetrated in the tissue and the counter electrode will depend on the surrounding tissue and will typically be less than the one for the segment facing air.

According to this embodiment the sensing unit 104 senses the number of electrode segments that are inserted in the body, and determines the insertion depth by way of this segment number, wherein each segment may have a longitudinal width of approximately 1-20 mm.

According to this embodiment of the present invention the segmentation also permits the control unit 108 to turn on/off various segments of the electrode depending for instance on the impedance as an indicator of the penetration depth of first electrode of the elongated hollow member. By turning off the segment at the air-skin interface of the elongated hollow member, skin burn effects can successfully be avoided, while simultaneously ensuring complete tract killing. The application of radio frequency energy may thus be optimized according to different positions or motions of the elongated hollow member with respect to the tissue surrounding the electrode.

According to an alternative embodiment of the present invention the elongated hollow member 102 comprises a coating of a dielectric material at the proximal or distal end, being an electrical insulator at low radio frequency frequencies for which frequencies the coated part of the first electrode cannot conduct electric current. Upon the usage of higher frequencies the impedance over the dielectric coating decreases, which enables the usage of the entire needle including the coated part.

In the following a few applications of the present invention are described. It should be mentioned that the principle characteristics and features of the present invention as described above in the detailed description of the embodiments are applicable in each one of the applications that will be described below.

Although the usage of a few features will be repeated in connection with the specific applications below, this is not intended to preclude the usage of other features are described above, as indicate in the above standing paragraph.

According to one preferred embodiment of the present invention, the arrangement 100 is arranged to be used in connection with fine needle aspiration (FNA). Within this application the anti-seeding technique is incorporated in an aspiration needle, being one example of an elongated hollow member 102, enabling the aspiration of aspirate of suspected tumour cells without the risk of seeding malignant cells and infectious matter upon both withdrawal and insertion of the aspiration needle in the needle track.

In the following, a FNA arrangement comprising anti-seeding features will be described in some detail.

According to one embodiment of the present invention the arrangement 100 comprises a tubular needle 102, being another example of an elongated hollow member.

The FNA needle to be inserted into the sampling site of the human or animal body, typically comprises a tubular member with a sharp distal end. According to one embodiment, the needle has an external diameter in the range of up to 3 mm and a length of 15-150 mm, depending on the tumour or sampling site.

The needle may furthermore comprise a first electrode positioned along the needle from the distal end of the needle until a region near the proximal end of the needle, which proximal end of the needle is electrically isolated from the radio frequency source.

If the needle is made of metal the exterior needle surface is preferably provided with an insulating or a dielectric material surrounding the needle near the proximal end of the needle, such that skin damage of the skin in direct contact with the needle, due to the heat of the needle upon application, can be effectively avoided. If dielectric material is used, impedance measurements to determine penetration depth variations can still be used.

As discussed above provision of alternatives such as a slidable insulating sheath or a segmented electrode can also be applied to avoid skin damage, with the advantage that the penetration depth can be varied with complete denaturation of the entire needle tract.

As earlier determined by the inventor facilitated punctuation of un-healthy tissue and an increased amount of aspirate may be achieved when applying a longitudinal motion and rotational motion to the aspiration needle. This motion inserts and retracts the needle periodically when being applied to the needle.

In order to avoid spreading of malignant tumour cells and infectious matter when for instance inserting/retracting the aspiration needle into a tissue that is healthy, a solution comprising the application of radio frequency energy is thus proposed.

According to another preferred embodiment of the present invention the arrangement 100 is an anti-seeding arrangement that is adapted for infusion of diagnostic or therapeutic substances. The infusion needle may in all other aspects be the same as the fine needle aspiration needle, as described above.

According to another preferred embodiment of the present invention the arrangement is an anti-seeding arrangement that is adapted for core biopsy. Within this application the anti-seeding technique is incorporated in a biopsy needle, being one example of the elongated hollow member, enabling the removal of a core biopsy of suspected tumour cells without the risk of seeding malignant cells or infectious matter in the needle track.

The core biopsy needle may comprise a tubular member and a solid member provided inside said tubular member having an outer diameter of up to 3.5 mm and length of 50-150 mm depending on the tumour site, according to one embodiment of the present invention. An outer diameter up to 4.5 mm and a length of 30-200 mm may however also be provided, according to an alternative embodiment. The solid member may be provided with a storage compartment at the distal end for the core biopsy sample. During sampling the tubular member is slid over the solid member, usually under spring load or the like, to cut off tissue material in the storage compartment.

According to one core biopsy embodiment, the solid member may be electrically connected to the tubular member, enabling anti-seeding properties of also the solid member.

Further, the gathering of tissue is often completed within a fraction of a second, for the reason of the tubular and solid member being spring loaded in relation to each other. Both of these aspects, periodic longitudinal motion and rapid tissue gathering, require a rapid anti-seeding procedure. In order to achieve an appropriate anti-seeding a triggered procedure comprising pulsed energy delivery is required, for which reason it is provided by the present invention.

In addition to the advantage of denaturing possible cancer cells and infectious matter in the needle track, application of radio frequency energy brings the advantage of stopping potential bleeding from the biopsy needle track, which becomes an even more important feature when using relatively coarse needles.

As explained above, embodiments comprising a slidable insulating sheath may be successfully applied in connection with core biopsy to avoid skin burn effects and to enable the optimizing the effective length of the first electrode.

According to yet another embodiment of the present invention a segmented electrode may also be used in connection to this application being core biopsy of the present invention, according to lines as stated above.

According to yet another embodiment of the present invention a dielectric coating may also be used in connection to this application being core biopsy of the present invention, according to lines as stated above.

According to another preferred embodiment of the present invention, the anti-seeding arrangement is arranged for treatment with radio frequency ablation of for instance malignant tissue. Within this embodiment of the present invention the elongated hollow member comprises a treatment ablation needle.

In one example of such a treatment ablation needle it comprises two parallel internal channels that are connected to each other near or at the distal end of the needle, for enabling a cooling media to flow through the channel to enable temperature regulation of the ablation needle.

The ablation needle further comprises a first electrode that according to a preferred embodiment is longitudinally sectioned in two parts. This enables optimization of the distal section for tumour ablation treatment whereas both parts may be activated during anti-seeding.

According to an alternative embodiment of the present invention the ablation needle is coated at the proximal or distal end with a dielectric material, being an electrical insulator at low radio frequency frequencies for which frequencies the coated part of the first electrode cannot conduct electric current to for example avoid tissue damage. Upon the usage of higher frequencies the impedance over the dielectric coating decreases, which enables the usage of the entire needle including the coated part for denaturising or impedance measuring purposes of the needle tract.

According to an alternative embodiment of the present invention, the ablation needle comprises a movable isolation sheath which may be slid in the longitudinal direction of the tubular needle 102 which results in a variation of the electrode length of the tubular needle 102. These embodiments thus enable optimization of the electrode length for both the ablation treatment and the anti-seeding procedure.

According to yet another embodiment the ablation needle comprises an electrode being sectioned in more than two electrodes.

Within the embodiments of the present invention as described above, the slidable sheath being used for skin burn protection, can be placed onto the skin surface by making use of, for example, a larger diameter of the proximal end in the form of a flange or a collar of the tubular member, enabling penetration depth measurements by measuring impedance.

According to an alternative embodiment of the present invention, the arrangement adapted for radio frequency ablation comprises numerous treatment electrodes which can be extended from the tubular member in an umbrella like configuration during the ablation treatment phase. Such an arrangement can be considered to comprise one treatment section of the extendable umbrella electrodes, whereas anti-seeding is applied to the entire tubular member, except for the proximal end of the member, optionally being electrically isolated from the radio frequency source.

According to another preferred embodiment of the present invention the arrangement is an anti-seeding arrangement that is adapted for minimally invasive surgery, inspection and sampling such as for example for endoscopic procedures.

During minimally invasive surgery or laparoscopy several tubular members in the form of trocars may be inserted from incisions and/or body openings of the patient. The trocars are typically used for inserting a camera, surgical instruments, illumination etc. into the site. Especially during excision of tumours the risk of tumour spread in the trocar ports is substantial.

The first electrode may for this reason be positioned along the tubular member as was described in connection to the fine needle aspiration embodiment. The surgical instruments that may be inserted in the trocar can optionally be electrically connected to the tubular member to enable anti-seeding if appropriate. The relative penetration depth between the trocar and the inserted instrument may be determined by measuring the impedance, or by mechanically, electromagnetically or acoustically determining the penetration distance.

During robot endoscopy the anti-seeding technique can be implemented for the tubular members of the stereo tactical excision system of the robot. By penetration depth measurements triggering of anti-seeding pulsing may be accomplished.

Application of slidable insulating sheaths may be used for this application also, bringing the same or similar advantageous as described above in connection to the other applications of the present invention.

The usage of segmented and coated electrodes may likewise be used for minimally invasive surgery, offering advantageous effects similar to the ones as described above.

The described present invention thus carries the following advantages:

Upon applying pulsed radio frequency bursts for anti-seeding of the tracks formed, the denaturation of cells occurs within a layer having the thickness of the order of a few cell layers surrounding the elongated tubular member. This is an advantage since it is desired not to affect cells outside of the track formed.

Another advantage is that the radio frequency bursts stop potential bleeding by denaturating the cells in the layer surrounding the elongated tubular member.

Yet another advantage is that the thickness of the layer to be denatured may be altered by using different power and pulse settings. It is further advantageous that the cell denaturation may be performed automatically, that is without manual intervention, and instantaneously, which results in minor tissue disturbances as compared to the usage of the equipment as disclosed in the prior art.

It is also advantageous that the radio frequency pulsing technique is able to denaturise the needle tract instantaneously during very fast instrument movements for example when using a spring loaded biopsy excision instrument or when using longitudinal vibration to decrease penetration resistance.

Still yet another advantage is that the automatic triggering enables denaturing of multiple tracts that may be created during insertion.

Still yet another advantage is that this invention enables denaturation of the whole track length.

Still yet another advantage is that this invention enables denaturation of infectious matter during insertion for example in transrectal procedures.

Another clear advantage is that the use of pulsed radio frequency energy results in the absence of substantial alteration of the sample in the tubular member, within the diagnostic embodiments of the present invention.

Application of sensing means for the detection of movement of the elongated hollow member together with the usage of radio frequency power creating an essentially instantaneous denaturation of tissue surrounding an anti-seeding electrode, provides a rapid arrangement for anti-seeding without being directed towards time consuming alternatives as presented by the prior art.

It is emphasized that this invention can be varied in many ways, of which the alternative embodiments above only are examples of a few. These different embodiments are hence non-limiting examples. The scope of the present invention, however, is only limited by the subsequently following claims.

The invention claimed is:

1. An arrangement adapted for biopsy, the arrangement comprising:
   an elongated hollow member to receive a biopsy sample,
      the elongated hollow member having:
         two ends and
         an electrode,
            the electrode including a plurality of segments,
            at least one portion of the electrode being arranged at least near one of the two ends of the elongated hollow member,
            the electrode being connectable to an electromagnetic field generator, and
         the elongated hollow member being arranged to be at least partly inserted into a human body or an animal body to receive the biopsy sample,
   sensing means arranged to:
      sense a movement of the elongated hollow member, and
   control means,
      the control means:
         arranged to control the electromagnetic field generator for delivering radio frequency bursts to the electrode of the elongated hollow member,
         being connectable to the electromagnetic field generator, and including trigger means to:
            trigger the electromagnetic field generator to deliver the radio frequency bursts when the sensing means senses the movement of the elongated hollow member, and
      the control means being to:
         turn off a particular segment, of the plurality of segments of the electrode, at an air-skin interface of the elongated hollow member based on an impedance between at least part of the electrode and a counter electrode.

2. The arrangement according to claim 1, where the sensing means is arranged to sense the movement optically, mechanically, acoustically, electrically, or electromagnetically.

3. The arrangement according to claim 1, where the sensing means comprises an impedance sensing means to sense the impedance between the at least part of the electrode and the counter electrode.

4. The arrangement according to claim 1, where the sensing means is further arranged to be coupled to the elongated hollow member.

5. The arrangement according to claim 1, where the counter electrode is arranged to be connected to the electromagnetic field generator and arranged to be positioned on the human body or the animal body.

6. The arrangement according to claim 1, where the sensing means is further arranged to sense the impedance between the counter electrode and the at least part of the electrode.

7. The arrangement according to claim 1, where the sensing means is further arranged to sense a distance from a reference point for the elongated hollow member to a surface of a tissue of the human body or the animal body into which the elongated hollow member is arranged to be at least partly inserted.

8. The arrangement according to claim 1, where the control means is further arranged to be connected to the sensing means.

9. The arrangement according to claim 1, where the control means is further arranged to control an operation of the electromagnetic field generator to deliver the radio frequency bursts from the electromagnetic field generator in dependence of the movement.

10. The arrangement according to claim 1, where the arrangement further comprises the electromagnetic field generator, and where the electromagnetic field generator is arranged to deliver the radio frequency bursts.

11. The arrangement according to claim 1, where the electrode is located at the one of the two ends of the elongated hollow member.

12. The arrangement according to claim 1, where the elongated hollow member comprises a region that is electrically insulated in relation to the electrode.

13. The arrangement according to claim 12, where the region that is electrically insulated in relation to the electrode is situated near another one of the two ends of the elongated hollow member.

14. The arrangement according to claim 12, where the region comprises a hollow insulating sheath that is longitudinally movable over the electrode.

15. The arrangement according to claim 1, where the electrode is longitudinally segmented into the plurality of segments.

16. The arrangement according to claim 1, where the elongated hollow member is coated with a dielectric material.

17. The arrangement according to claim 16, where the radio frequency bursts are generated at one or more radio frequencies.

18. The arrangement according to claim 1, where the elongated hollow member comprises a needle arranged for fine needle aspiration or injection.

19. The arrangement according to claim 1, where the elongated hollow member further comprises a solid insertable member, and where the elongated hollow member and the solid insertable member are arranged for the biopsy.

20. The arrangement according to claim 1, where the elongated hollow member is arranged for radio frequency ablation of a tissue of the human body or the animal body.

21. The arrangement according to claim 1, where the elongated hollow member is arranged for endoscopic operations.

22. The arrangement according to claim 1, where the movement includes a retraction of the elongated hollow member.

23. The arrangement according to claim 1, where the movement includes an insertion of the elongated hollow member into the human body or the animal body.

* * * * *